(12) United States Patent
Maeda et al.

(10) Patent No.: US 8,234,939 B2
(45) Date of Patent: Aug. 7, 2012

(54) SAMPLE INTRODUCTION METHOD

(75) Inventors: Yoshiaki Maeda, Kyoto (JP); Shuzo Maruyama, Kyoto (JP); Kenichi Yasunaga, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 306 days.

(21) Appl. No.: 12/667,677

(22) PCT Filed: Sep. 24, 2008

(86) PCT No.: PCT/JP2008/067198
§ 371 (c)(1),
(2), (4) Date: Jan. 4, 2010

(87) PCT Pub. No.: WO2009/041441
PCT Pub. Date: Apr. 2, 2009

(65) Prior Publication Data
US 2010/0326215 A1 Dec. 30, 2010

(30) Foreign Application Priority Data

Sep. 28, 2007 (JP) ................................ 2007-256174

(51) Int. Cl.
*B01L 3/02* (2006.01)
(52) U.S. Cl. .................................................. 73/864.21
(58) Field of Classification Search ........................ None
See application file for complete search history.

(56) References Cited

U.S. PATENT DOCUMENTS

| | | | | |
|---|---|---|---|---|
| 4,939,943 A | * | 7/1990 | Strohmeier | 73/864.21 |
| 5,101,673 A | * | 4/1992 | Uffenheimer et al. | 73/864.22 |
| 6,734,424 B2 | * | 5/2004 | Lennon et al. | 250/288 |

FOREIGN PATENT DOCUMENTS

| | | |
|---|---|---|
| JP | H03-19962 | 2/1991 |
| JP | 06-148157 | 5/1994 |
| JP | 10-170488 | 6/1998 |
| JP | 2001-255315 | 9/2001 |
| JP | 2004-085499 | 3/2004 |
| JP | 2004-215118 | 7/2004 |
| JP | 2006-038809 | 2/2006 |
| JP | 3129670 | 3/2007 |

* cited by examiner

*Primary Examiner* — Robert R Raevis
(74) *Attorney, Agent, or Firm* — J.C. Patents

(57) ABSTRACT

A sample introduction method for reducing carry-over is provided. After a sample introduction device in a total volume injection method draws a proper amount of a sample solution from a sample container and further draws a solution with the same composition as a mobile phase solution with a needle 24, the needle 24 is inserted into an injection port 25. When flow paths are switched to communicate a liquid feeder, a sample loop 23, the needle 24, the injection port 25, and a separation/detection section, the solution with the same composition as the mobile phase solution is forced into a gap between the injection port 25 and the needle 24. Therefore, the samples squeezed out of a tip section of the needle 24 during the switching of the flow paths are prevented from being forced into the gap between the needle 24 and the injection port 25.

7 Claims, 7 Drawing Sheets

(a)

(b)

(c)

(d)

(a) First status — Second status (b) First status — Second status (c)

SAMPLE INTRODUCTION METHOD

BACKGROUND OF THE INVENTION

1. Field of the Invention

The present invention generally relates to a sample introduction method for guiding liquid samples into an analytical equipment, in particular, to a sample introduction method using a sample introduction device including a needle and an injection port connected to a flow path switching valve.

2. Description of Related Art

In order to analyze a plurality of samples, a sample introduction device for automatically guiding samples into an analytical equipment such as a liquid chromatograph in a specified sequence is adopted. FIG. 2(a) is a schematic view of a liquid chromatograph. The liquid chromatograph is formed of a liquid feeder 10, a sample introduction device 20, a separation/detection section 30, and a control/resolution section 40. The sample introduction device 20 is disposed between the liquid feeder 10 and the separation/detection section 30. The separation/detection section 30 includes an analysis column 31 and a detector 32, and various flow paths are formed for actual analysis purposes, thereby functioning as an analysis section. The liquid feeder 10, the sample introduction device 20, and the separation/detection section 30 are controlled by the control/resolution section 40. After receiving a signal from the detector 32, the control/resolution section 40 performs qualitative/quantitative resolution on the samples and saves the resolution data or files and outputs an analysis report.

The sample introduction device has the following two injection methods: a "total volume injection method" of injecting all measured samples from a sample container and a "partial injection method" of filling and injecting a part of the measured samples from the sample container into a sample loop (Patent Documents 1, 2, and Non-patent Document 1). In the fields that only quite a few samples can be collected, the total volume injection method is widely applied for analysis for not wasting the collected samples.

FIG. 2(b) is a schematic view of flow paths inside the sample introduction device 20 for the total volume injection method. The sample introduction device 20 forms the flow paths centered with a six-port two-position valve 21 and a six-position valve 22. A flow path of a mobile phase solution from the liquid feeder 10 into the sample introduction device 20 is first connected to one port of the six-port two-position valve 21. A flow path, which is from the upstream side of the liquid feeder 10 and a flow path, which is toward the downstream side of the separation/detection section 30 communicate with each other through a sample loop 23, a needle 24 disposed at a tip section of the sample loop 23 and an injection port 25 inserted with the needle 24. Therefore, all samples filled in the needle 24 to the sample loop 23 are guided into the separation/detection section 30. The six-position valve 22 is connected to a flow path in communication with a metering pump 26 for drawing a cleaning fluid from a cleaning fluid container or drawing samples from a sample container 28, and a flow path in communication with a cleaning port 27 provided for the insertion of the needle 24 so as to clean the needle. Moreover, the needle 24 and the sample loop 23 are communicated with the flow path of the metering pump 26 through the six-port two-position valve 21. In addition, the six-port two-position valve 21 switches the flow path of the mobile phase solution pressurized by the liquid feeder 10 and is thus called a "high pressure valve". The six-position valve 22 is not connected to a flow path applied with a relatively high pressure and is thus called a "low pressure valve".

Accordingly, in this specification, the six-port two-position valve may be referred to as the "high pressure valve" and the six-position valve may be referred to as the "low pressure valve".

To facilitate the understanding, a flow path switching valve, such as the high pressure valve 21 or the low pressure valve 22, is illustrated. In the flow path switching valve, a stator surface disposed with holes is joined to a rotor surface disposed with grooves, and each groove on the rotor surface (rotor groove) communicates with two holes on the stator surface (stator holes). The rotor rotates to make the rotor surface slide relative to the stator surface, so that a relative position between the rotor groove and the stator holes is changed, thereby switching a communication status between one stator hole and the other stator holes. Moreover, the stator holes are in communication with the ports disposed on the flow path switching valve respectively and each port is connected to a flow path. Therefore, when the rotor rotates to cause a change of the relative position between the rotor groove and the stator holes, a communication status of the flow path connected to the port is switched.

FIGS. 7(a) to 7(c) are diagrams respectively showing communication statuses of a joint surface of the high pressure valve 21 and the low pressure valve 22. The high pressure valve 21 in FIG. 7(a) is used for switching the flow paths in any of the two statuses. The high pressure valve 21 includes stator holes (a, b, c, d, e, and f) and arc-shaped rotor grooves (X, Y, and Z) centered with a rotation axis of the rotor. The high pressure valve 21 switches between a first status and a second status. In the first status, the rotor groove X communicates with the stator holes a and b, the rotor groove Y communicates with the stator holes c and d, and the rotor groove Z communicates with the stator holes e and f. In the second status, the rotor groove X communicates with the stator holes b and c, the rotor groove Y communicates with the stator holes d and e, and the rotor groove Z communicates with the stator holes f and a. In FIG. 2(b), in the high pressure valve 21, a port in communication with the stator hole a is connected to a flow path in communication with the needle 24 through the sample loop 23, a port in communication with the stator hole b is connected to a flow path in communication with the liquid feeder 10, a port in communication with the stator hole c is connected to a flow path in communication with the separation/detection section 30, and a port in communication with the stator hole d is connected to a flow path in communication with the injection port 25. The flow paths connected to a port in communication with the stator hole e and a port in communication with the stator hole f are determined according to the actual purposes and applications. When the high pressure valve 21 is in the first status, the flow path, which is from the upstream side of the liquid feeder 10 and the flow path, which is toward the downstream side of the separation/detection section 30 are communicated through the sample loop 23, the needle 24, and the injection port 25 (this status is also referred to as an "injection status"). When the high pressure valve 21 is in the second status, the flow path, which is from the upstream side of the liquid feeder 10 and the flow path, which is toward the downstream side of the separation/detection section 30 are not communicated through the sample loop 23, the needle 24, and the injection port 25 (this status is also referred to as a "load status").

It takes tens of milliseconds to hundreds of milliseconds to switch between the first status and the second status. Generally, during this period, none of the stator holes are communicated, and in certain cases, a relatively long rotor groove is formed deliberately as mentioned in Non-patent Document 1. FIG. 7(b) depicts a high pressure valve in Non-patent Document 1, in which the rotor groove X is set longer than another rotor grooves Y and Z. The high pressure valve 21' performs the following functions, which are using a metering pump to repeatedly draw and discharge samples and filling the samples in a sample loop having a volume greater than or equal to that of the metering pump while remaining in the load status. The high pressure valve 21' is obtained through improvement on the structure disclosed in Patent Document 2.

The low pressure valve 22 in FIG. 7(c) is used for switching between six communication statuses, so as to enable a common port to be communicated with the other ports and/or enable various ports to be communicated with each other. The low pressure valve 22 includes stator holes (h, p, r, s, t, and u) and rotor grooves (V and W). The stator hole h is always connected to one end of the rotor groove V and is also in communication with the common port of the low pressure valve 22. The metering pump 26 or the cleaning port 27, the cleaning fluid container are connected to the other ports of the low pressure valve 22 and are also connected to the ports of the high pressure valve 21, so as to be in communication with the needle 24 and the injection port 25 etc. In FIG. 2(b), the common port in communication with the stator hole h is connected to the flow path connected with the metering pump 26. Samples are drawn or discharged from the sample container 28 and the cleaning fluid is drawn or discharged through the switching of the low pressure valve 22. Further, in order to accurately draw with the metering pump 26, the pressure in a sampling flow path (through the needle 24 and the sample loop 23) is at the atmospheric pressure, or other measures are taken. In addition, a low pressure valve without a common port is used in Non-patent Document 1.

Patent Document 1: Japanese Patent Publication No. H06-148157

Patent Document 2: Japanese Patent Publication No. H10-170488

Non-patent Document 1: "HPLC//LCtalk No. 46 TEC, INJECTION METHODS OF SAMPLE INTRODUCTION DEVICE (COMPARISON BETWEEN TOTAL VOLUME INJECTION METHOD AND PARTIAL INJECTION METHOD)", Shimadzu Corporation, online, http://www.an-.shimadzu.co.jp/support/lib/lctalk/46/46tec.htm, searched on Sep. 25, 2007.

In the total volume injection method shown in FIG. 2(b), when the high pressure valve 21 is in the load status, a specified volume of samples are drawn from the sample container 28 through the needle 24 and then filled into the sample loop 23 connected to a bottom section of the needle 24. Thereafter, the needle 24 is moved to the cleaning port 27 to have its outer surface cleaned. Afterward, the needle 24 is inserted into the injection port 25, and the high pressure valve 21 is switched to the injection status. The circulation of the mobile phase solution inside the sample loop 23 forces the samples filled in the sample loop 23 out and guides all the samples into the separation/detection section 30. For the guided samples, the high pressure valve remains in the injection status till the analysis is over. That is, during the analysis, the mobile phase solution keeps flowing inside the needle 24. In other words, the mobile phase solution remains in a cleaning status inside the needle 24.

Although the outer side of the needle 24 is cleaned at the cleaning port 27 and the inner side thereof is cleaned with the mobile phase solution, the problem of carry-over may still occur. The so-called carry-over means a phenomenon that a part of the injected samples are left behind and affect the next round of analysis. Although the carry-over is greatly alleviated through the surface treatment of the needle, the cleaning of the needle, and the change of the shape of the injection port, the problem still remains. Meanwhile, with the development of ultra-micro analysis and highly sensitive detection in recent years, the problem is growing worse. Therefore, the carry-over impedes the accurate analysis on the volume of samples drawn from the sample container 28.

After careful researches, the inventor of the present invention has identified the reason why carry-over still occurs even if the needle 24 is cleaned in the process of switching the high pressure valve from the load status to the injection status.

The switching of the flow paths is realized through the operation of the high pressure valve 21 and the processes for forming of the status in which the rotor grooves communicate with the stator holes are greatly related through the operation. As shown in FIG. 7(a), even if the three rotor grooves have the same length, the rotor surface and the stator surface sliding repeatedly may still be abraded due to long-time use; thus, the sections for forming the rotor grooves or the stator holes may be damaged. According to the different damaged sections, a status having the same effect as that formed with a relatively longer rotor groove is obtained. As a result, flow paths communicated in a time sequence different from the original one are generated. According to different damaged sections and the degrees of the damage, the high pressure valve 21 becomes a valve the same as shown in FIG. 7(b). As described above, the high pressure valve in FIG. 7(b) is applicable for processing samples having a large volume (from hundreds of μl to several ml) exceeding a 1-stroke volume of the metering pump 26, but is not suitable for processing a minute volume of the samples.

FIGS. 6(a) to 6(d) show the flowing directions of the samples at a circumference of an insertion section of the needle 24 and the injection port 25 as well as the movement of the samples inside the needle 24 in a period from the moment that the high pressure valve 21' is switched to the injection status immediately after the needle 24 is inserted into the injection port 25 till the moment that all the samples flow to the downstream side. FIGS. 6(a) to 6(d) also show a generation mechanism of carry-over caused by the abraded high pressure valve 21'.

First of all, FIG. 6(a) shows a status that the needle 24 is inserted into the injection port 25 after the sample solution is measured. Till the high pressure valve 21' is switched from the load status to the injection status, the samples are located at a tip section inside the needle 24 and the needle 24 is filled with the mobile phase solution in a manner of holding the samples.

Referring to FIG. 6(b), during the switching from the load status to the injection status, only the rotor groove X communicates with the stator holes a and b among the three rotor grooves, enabling the liquid feeder 10 and the needle 24 to communicate with each other. At this time, a part of the samples are forced out of the tip section of the needle 24 into the injection port 25 under the pressure of the liquid feeder 10. In this case, as the injection port 25 does not communicate with the separation/detection section 30, and the samples cannot flow to the downstream side, so that the part of the samples under the pressure of the liquid feeder are forced into a gap between the tip section of the needle 24 and the injection port 25 (FIG. 6(c)). The section marked by a circle in FIG. 6(c) is an amplified view of the tip section of the needle. A gap exists between the tip section of the needle 24 after taper machining and an inner wall of the injection port 25 substantially formed perpendicularly thereto, so that the samples are forced into the gap.

Afterward, the injection port 25 is in communication with the separation/detection section 30, and the samples are guided into the separation/detection section 30 under the influence of the mobile phase solution delivered by the liquid feeder 10. However, the portions of the samples that are forced into the gap are not guided into the separation/detection section 30, but are left in the injection port 25 instead (FIG. 6(d)). That is, as for the carry-over that still occurs even if the needle 24 is cleaned, during the switching from the load status to the injection status, the communication between the needle 24 and the liquid feeder 10 (the stator holes a and b communicate with each other through the rotor groove X) results in carry-over more easily, when compared with the communication between the injection port 25 and the separation/detection section 30 (the stator holes c and d communicate with each other through the rotor groove Y).

SUMMARY OF THE INVENTION

The present invention is directed to reducing the carry-over by decreasing a volume of samples forced into a gap in an insertion section of a needle and an injection port.

The present invention provides a sample introduction method using a sample introduction device including a flow path switching valve and a moving mechanism. The method includes the following steps. The flow path switching valve is switched from a first status to a second status. The moving mechanism is actuated to move a needle to a position for drawing samples and draw a specified volume of the samples with the needle. The moving mechanism is actuated to move the needle away from the position for drawing samples and insert the needle into an injection port. The flow path switching valve is connected to a flow path in communication with a liquid feeder for delivering a solution, a flow path in communication with a sample loop provided with the needle at a tip section, a flow path in communication with an analysis section for analyzing samples, and a flow path in communication with the injection port inserted with the needle. The flow path switching valve switches between the first status, in which the liquid feeder is in communication with the analysis section through the sample loop and the injection port, and the second status, in which the liquid feeder is in communication with the analysis section not through the sample loop and the injection port. The moving mechanism enables the needle to move between the position for drawing samples and the injection port. Before the moving mechanism is actuated to move the needle away from the position for drawing samples and insert the needle into the injection port, the samples inside the needle are drawn into the sample loop. A solution or a cleaning fluid with the same composition as the mobile phase solution or air is drawn through an operation of drawing the samples in the needle into the sample loop.

Through the drawing of the samples inside the needle, the liquid surface of the samples in the needle drawn from the sample container is moved from near a tip section of the needle to the side of the sample loop. A layer with a different composition from the samples (or having the same composition as the mobile phase solution or air) is formed between the liquid surface of the samples and the tip section of the needle. Afterward, the needle is inserted into the injection port. If the automatic sample introduction device has a cleaning port, the needle may be cleaned before being inserted into the injection port.

[Effect of the Invention]

When the flow paths are switched to guide a sample into the separation/detection section at the downstream side, the sample remained between the tip section of the sample needle and the injection port is decreased, thereby reducing the circumstance that the residual sample and a next sample are guided together. In other words, the problem of carry-over is alleviated. Moreover, accurate quantification may be performed on the samples and the precision of the analysis is improved due to the alleviation of the carry-over. In ultra-micro analysis that is greatly affected by the carry-over, the precision of the analysis is significantly improved. In addition, even for the sample introduction device in the prior art, the method of the present invention may also be implemented by merely changing the sequence of guiding the samples from the sample container.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

LIST OF THE SYMBOLS

Figure 1:
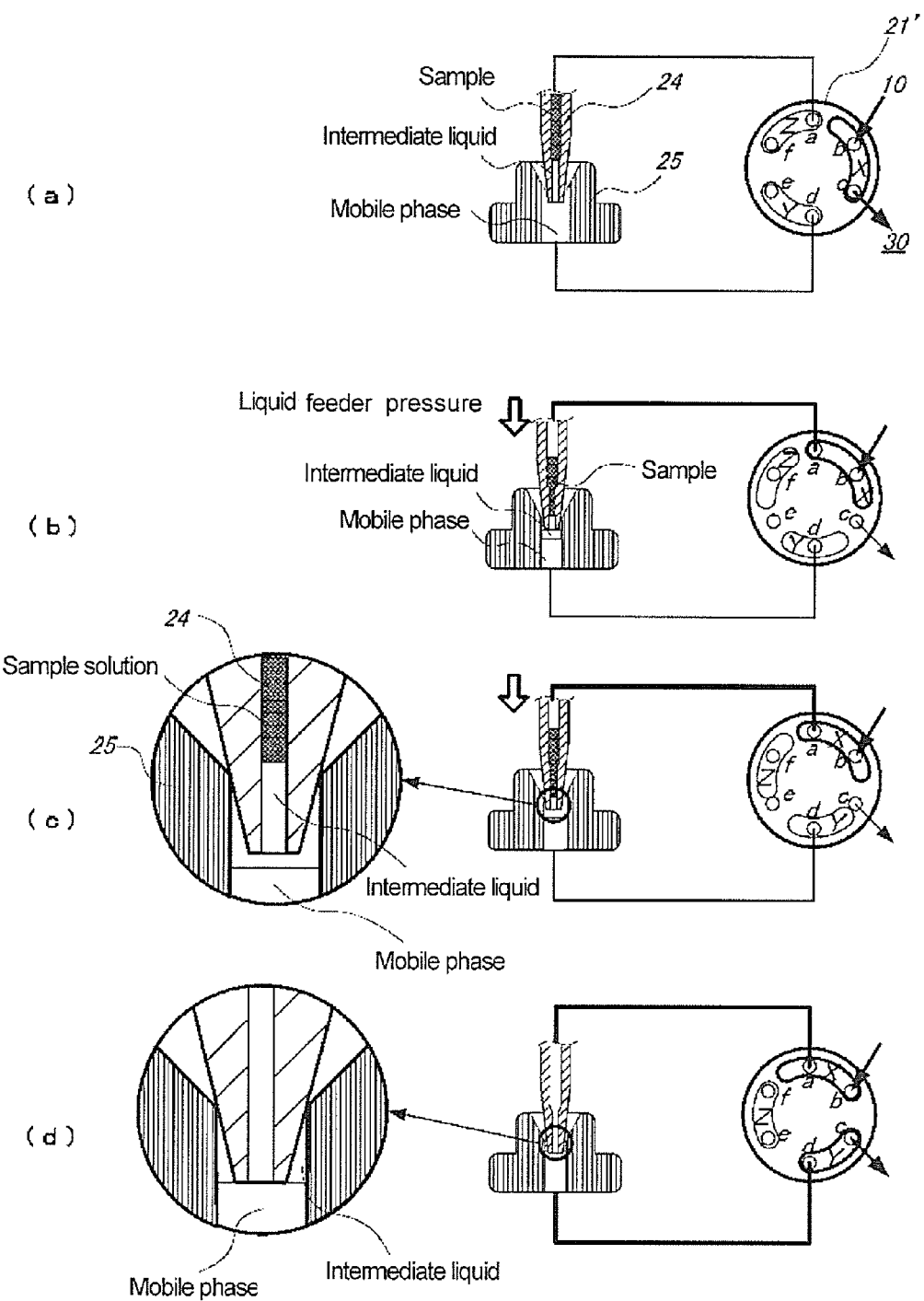
FIGS. 1(a) to 1(d) are diagrams illustrating a status of samples at an insertion section of a sampling and injection port in a sample introduction method according to the present invention.

| | |
|---|---|
| 10 | liquid feeder |
| 20 | sample introduction device |
| 21 | 6-port 2-position valve (high pressure valve) |
| 21' | special high pressure valve (or a deteriorated high pressure valve) |
| 22 | 6-position valve (low pressure valve) |
| 23 | sample loop |
| 24 | needle |
| 25 | injection port |
| 26 | metering pump |
| 27 | cleaning port |
| 28 | sample container |
| 29 | intermediate liquid container |
| 30 | separation/detection section |
| 31 | column |
| 32 | detector |
| 40 | control/resolution section |

DESCRIPTION OF THE EMBODIMENTS

Reference will now be made in detail to the present embodiments of the invention, examples of which are illustrated in the accompanying drawings. Wherever possible, the same reference numbers are used in the drawings and the description to refer to the same or like parts.

Figure 7:
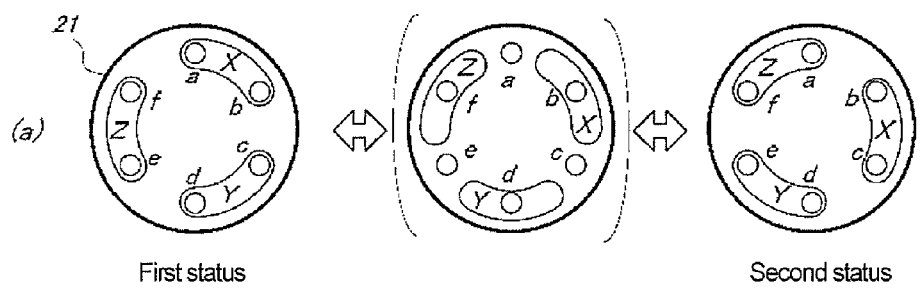
FIGS. 7(a) to 7(c) are diagrams illustrating switched statuses of a high pressure valve (a six-port two-position valve) and a low pressure valve (a six-position valve).
Figure 7:
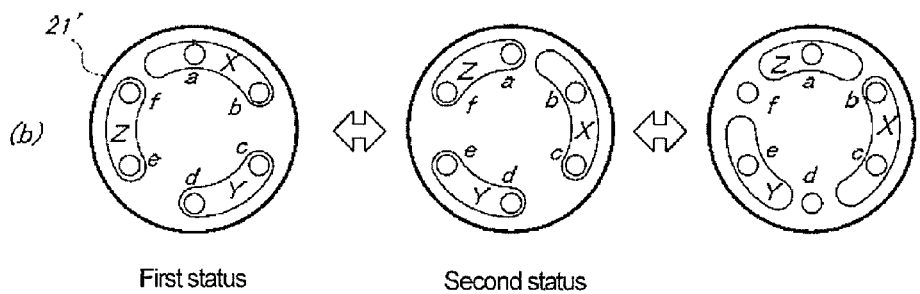
Figure 7:
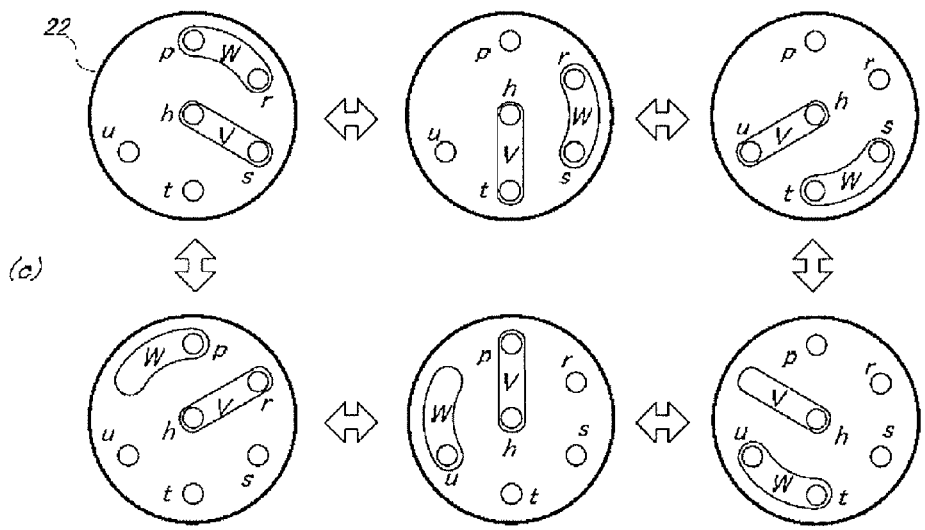

A sample introduction method of the present invention is illustrated below with the accompanying drawings. In the present invention, only the guiding of the samples from a sample container to an analysis flow path is changed, and the configuration of the flow paths or the flow path switching valve is the same as that in the prior art. The high pressure valve 21 may be the special valve as shown in FIG. 7(b) or a valve deteriorated to the same status.

Figure 2:
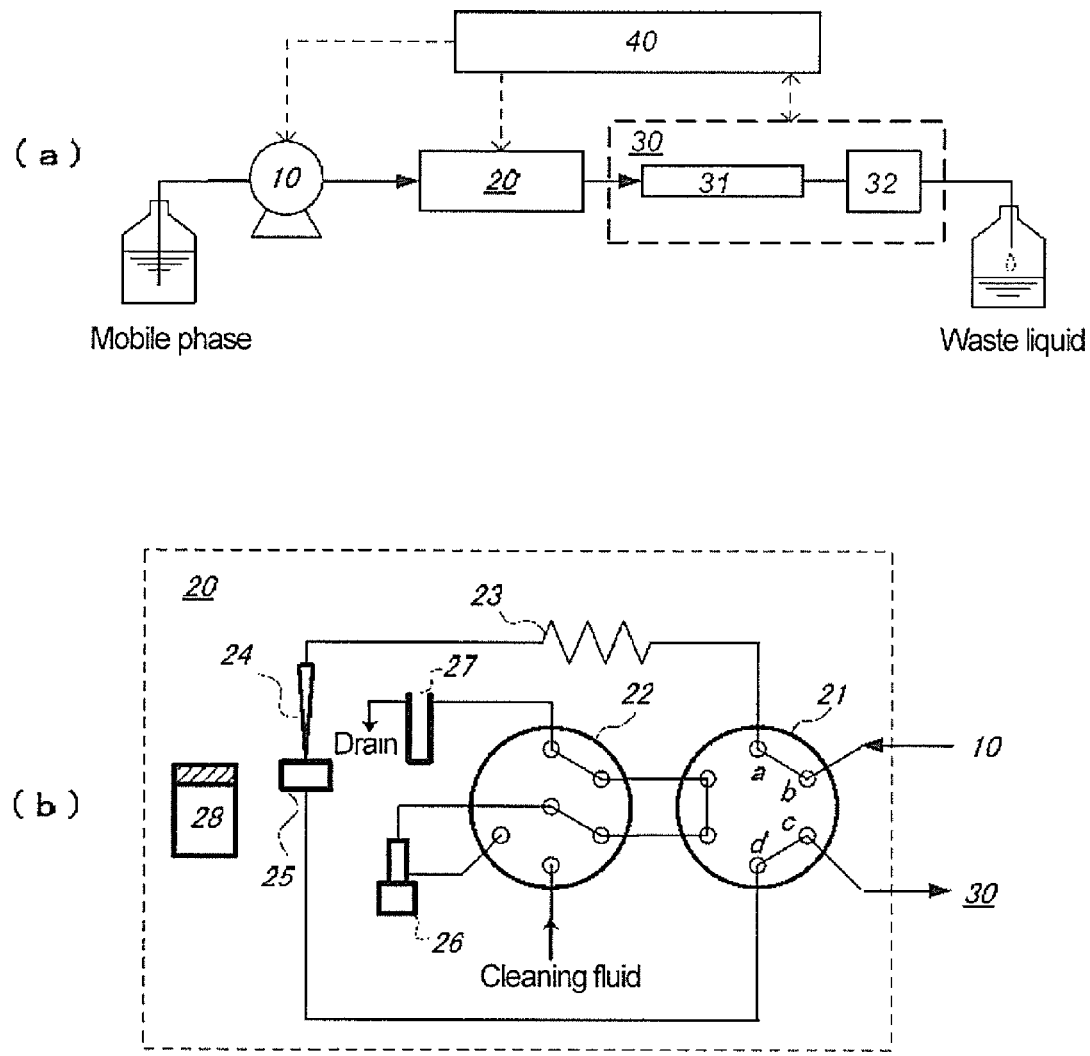
FIG. 2(a) is a schematic view of a structure of a liquid chromatograph.
FIG. 2(b) is a schematic view of a flow path of a sample introduction device in a total volume injection method.
Figure 3:
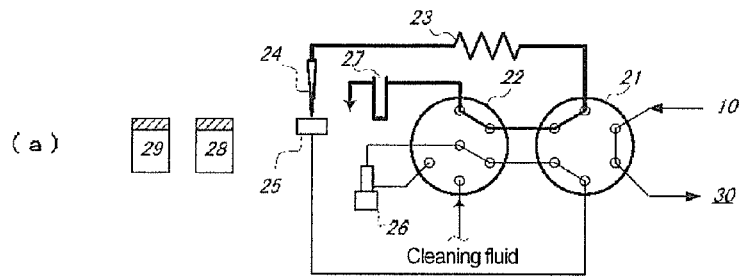
FIG. 3(a) shows a flow path in a standby status.
FIG. 3(b) shows a flow path when samples are drawn and a needle is cleaned.
FIG. 3(c) shows a flow path when an intermediate liquid is drawn.
FIG. 3(d) shows a flow path when the samples are guided.
Figure 3:
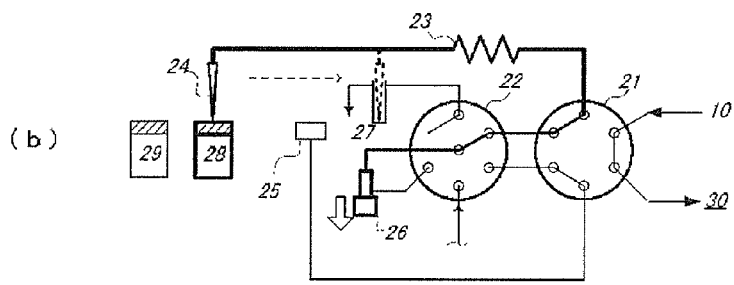
Figure 3:
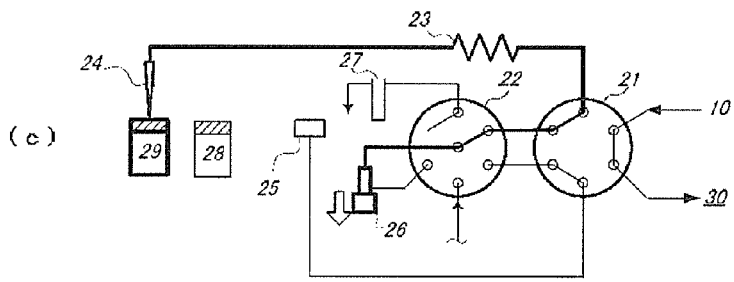
Figure 3:
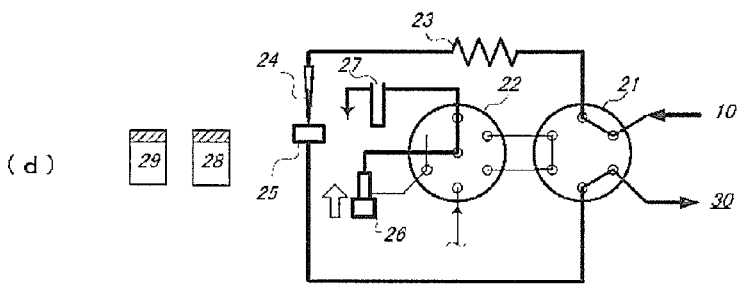

In a period of drawing samples from the sample container 28 (in a standby status before new samples are guided), the communication status inside the sample introduction device 20 is shown in FIG. 2(b), and the high pressure valve 21 is in an injection status. As the liquid feeder 10 delivers the mobile phase solution with a high pressure (several MPa to tens of MPa), before the samples are drawn, the pressure of the sampling flow path is at the atmospheric pressure. That is, as shown in FIG. 3(a), the high pressure valve 21 turns into a load status. In another aspect, the low pressure valve 22 is in a status in which the needle 24, the sample loop 23, and the cleaning port 27 are in communication and the injection port 25 and the metering pump 26 are in communication. Therefore, the sampling flow path is open to the atmospheric pressure.

Then, referring to FIG. 3(b), the low pressure valve 22 rotates to enable the needle 24 to communicate with the metering pump 26 through the sample loop 23, the high pressure valve 21, and the low pressure valve 22. Moreover, a moving mechanism (not shown) is employed to allow the needle 24 to depart from the injection port 25 and immerse into the sample solution inside the sample container 28. Then, the metering pump 26 operates to draw a required volume of the sample solution from the sample container 28. After the required volume of the samples are drawn, referring to the dotted line in FIG. 3(b), the needle 24 is inserted into the cleaning port 27 to have its outer side cleaned with the cleaning fluid stored in the cleaning port 27.

Thereafter, referring to FIG. 3(c), the needle 24 is moved to an intermediate liquid container 29 filled with a liquid with the same composition as the mobile phase solution (referred to as an "intermediate liquid" for the purpose of illustration). The needle 24 draws the intermediate liquid from the intermediate liquid container 29. The drawn amount of the intermediate liquid may be 0.5% to 2% of an internal volume of the sample loop 23. At this time, the drawn volume of the samples and the drawn amount of the intermediate liquid may not exceed the volume of the sample loop 23. Moreover, the liquid feeder 10 is a gradient device for delivering a liquid in which the composition changes with time. When the composition of the liquid changes from Liquid A (for example, pure water) to Liquid B (for example, acetonitrile), Liquid A (pure water) needs to be prepared as the intermediate liquid. Alternatively, the liquid in the cleaning port 27 may also be used to replace the intermediate liquid in the intermediate liquid container 29. The liquid in the cleaning port 27 is more desirable as it may not be contaminated due to proper replacement and can be connected to a container for supplying the mobile phase solution to the liquid feeder 10. Moreover, it is acceptable to draw in the intermediate liquid during the movement of the needle 24, and it is also acceptable to draw in air. After the samples and the intermediate liquid or air are drawn in sequence, the needle 24 is moved and inserted into the injection port 25, and the high pressure valve 21 is switched to the injection status.

FIGS. 1(a) to 1(d) show the flowing directions of the liquid inside the needle 24 of a period from the moment that the needle 24 is inserted into the injection port 25 till the moment that the high pressure valve 21 is switched from the load status to the injection status. For the ease of illustration, the high pressure valve 21 is illustrated as the aforementioned special valve.

Referring to FIG. 1(a), after the needle 24 is inserted into the injection port 25, as the intermediate liquid exists in the tip section of the needle 24, the samples are kept inside the needle 24 (at the side of the high pressure valve 21). Referring to FIG. 1(b), when the high pressure valve 21 starts to be switched, once the flow path between the needle 24 and the liquid feeder 10 opens up, and the intermediate liquid is forced out of the tip section of the needle 24.

Referring to FIG. 1(c), the intermediate liquid is forced into a gap between the needle 24 and the injection port 25 instead of flowing to the downstream side. However, the samples are still retained in the needle 24.

Afterwards, referring to FIG. 1(d), the injection port 25 is in communication with the separation/detection section 30. Under the pressure of the mobile phase solution supplied by the liquid feeder 10, the samples that are already drawn in the sample loop 23 are guided from the needle 24 into the separation/detection section 30 at the downstream side through the injection port 25. The guided samples are analyzed in the injection status and the mobile phase solution keeps flowing to the insertion section of the needle 24 and the injection port 55, so that the samples may not remain in the gap.

During the analysis, as shown in FIG. 3(d), the low pressure valve 22 rotates to enable the metering pump 26 to communicate with the cleaning port 27. The metering pump 26 operates to discharge the cleaning fluid in the flow path of the plunger pump 22 to the cleaning port 27, and further to discharge the cleaning fluid to a drain.

When the high pressure valve 21 is switched from the load status to the injection status in the above manner, a small amount of the solution at the tip section of the needle 24 is forced into the injection port 25. The liquid forced into the gap formed by inserting the needle 24 in the injection port 25 has the same composition as the mobile phase solution. Therefore, the liquid forced into the gap may not result in the problem of carry-over. Moreover, when air is drawn in, most of the air is dissolved in the mobile phase solution and flows to the downstream side, so that the space occupied by the air is substituted by the mobile phase solution; in this case, the carry-over may not occur.

The sample introduction method of the present invention is described above. Moreover, an actual measurement example showing the effect of reducing the carry-over by using the sample introduction device of the present invention is given below. In order to demonstrate a carry-over volume herein, a caffeine aqueous solution is adopted as a sample for analysis and an area $\alpha$ of a peak of a chromatogram is obtained for the caffeine aqueous solution. Then, the same analysis is conducted on a liquid having the same composition as the mobile phase solution (a blank sample), so as to calculate an area $\beta$ of a peak within the same holding time as the caffeine aqueous solution. Afterwards, a ratio of $\beta$ to $\alpha$ is determined to be a carry-over volume. The actual measurement is employed for the sample introduction method in the prior art and the sample introduction method of the present invention.

[Analysis Conditions]

| | |
|---|---|
| Sample | 250 mg/L Caffeine Aqueous Solution |
| Sample Injection Volume | 10 μL |
| Sample Drawing Velocity | 15 μL/s |
| Mobile Phase Composition | Water:Methanol = 4:1 |
| Flow Rate | 1.0 mL/min |
| Column | Reverse-phase Column (Inner Diameter 3 mm × Length 50 mm) |
| Detector | UV-visible Spectro-photometric Detector (Detection Wavelength: 272 nm) |

Figure 4:
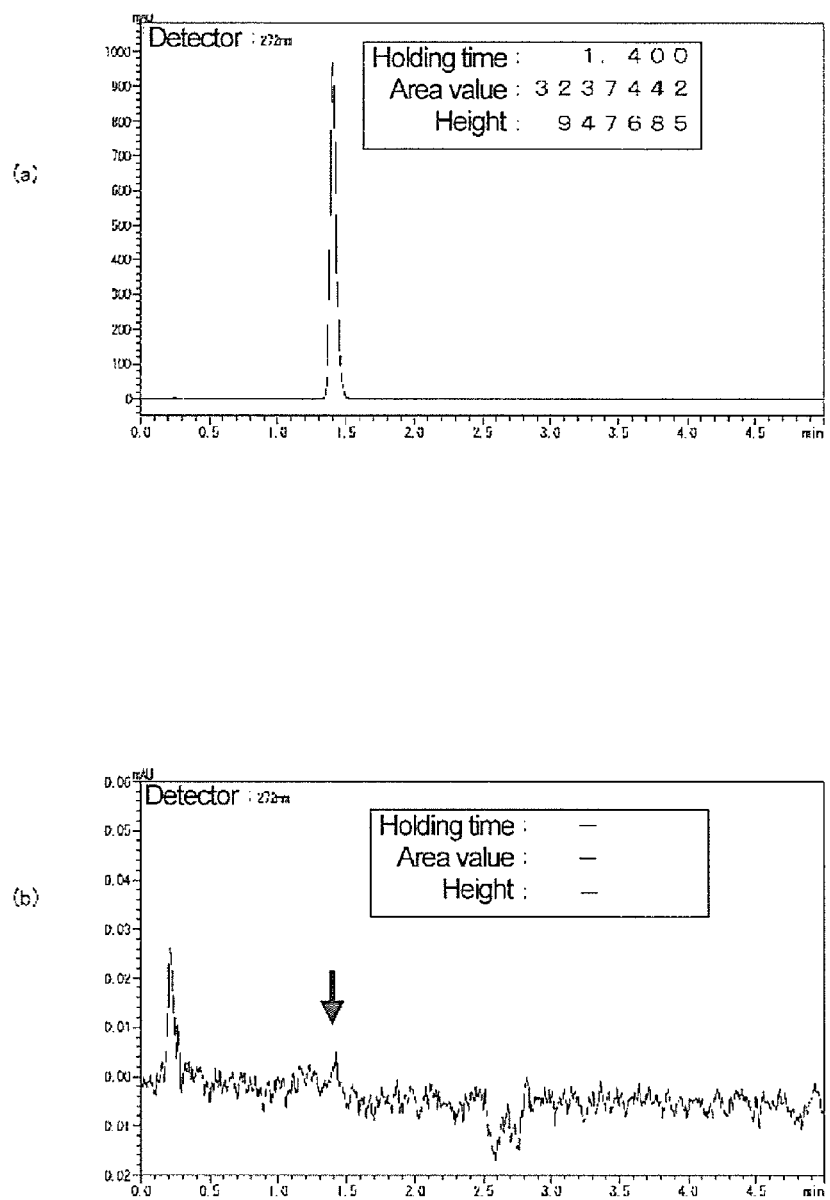
FIGS. 4(a) to 4(b) are chromatograms of a carry-over test obtained through the sample introduction method of the present invention.

FIGS. 5(a) and 5(b) are chromatograms obtained through the sample introduction method in the prior art. FIG. 5(a) is a chromatogram of the caffeine aqueous solution, and FIG. 5(b) is a chromatogram of the blank sample. FIGS. 4(a) and 4(b) are chromatograms obtained through the sample introduction method of the present invention. FIG. 4(a) is a chromatogram of the caffeine aqueous solution, and FIG. 4(b) is a chromatogram of the blank sample. The scales on the time axes of all the chromatograms, that is, the horizontal axes, are the same. However, as for the scales on the intensity axes, that is, the longitudinal axes, the scales in FIGS. 5(b) and 4(b) are much smaller than those in FIGS. 5(a) and 4(a).

Figure 5:
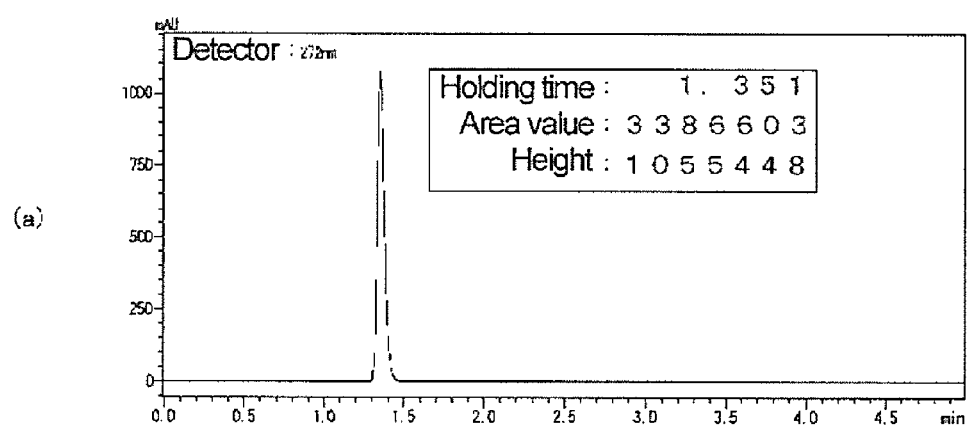
FIGS. 5(a) to 5(b) are chromatograms of a carry-over test obtained through the sample introduction method in the prior art.
Figure 5:
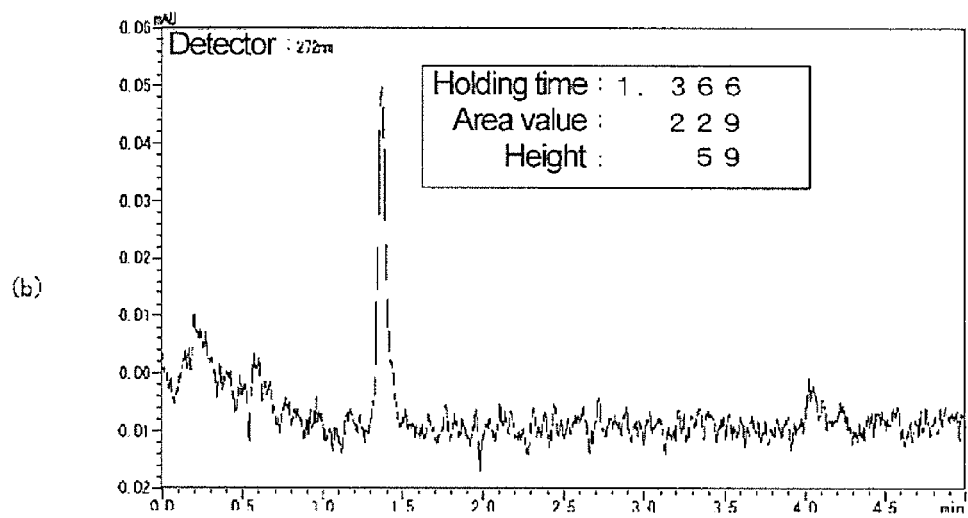
Figure 6:
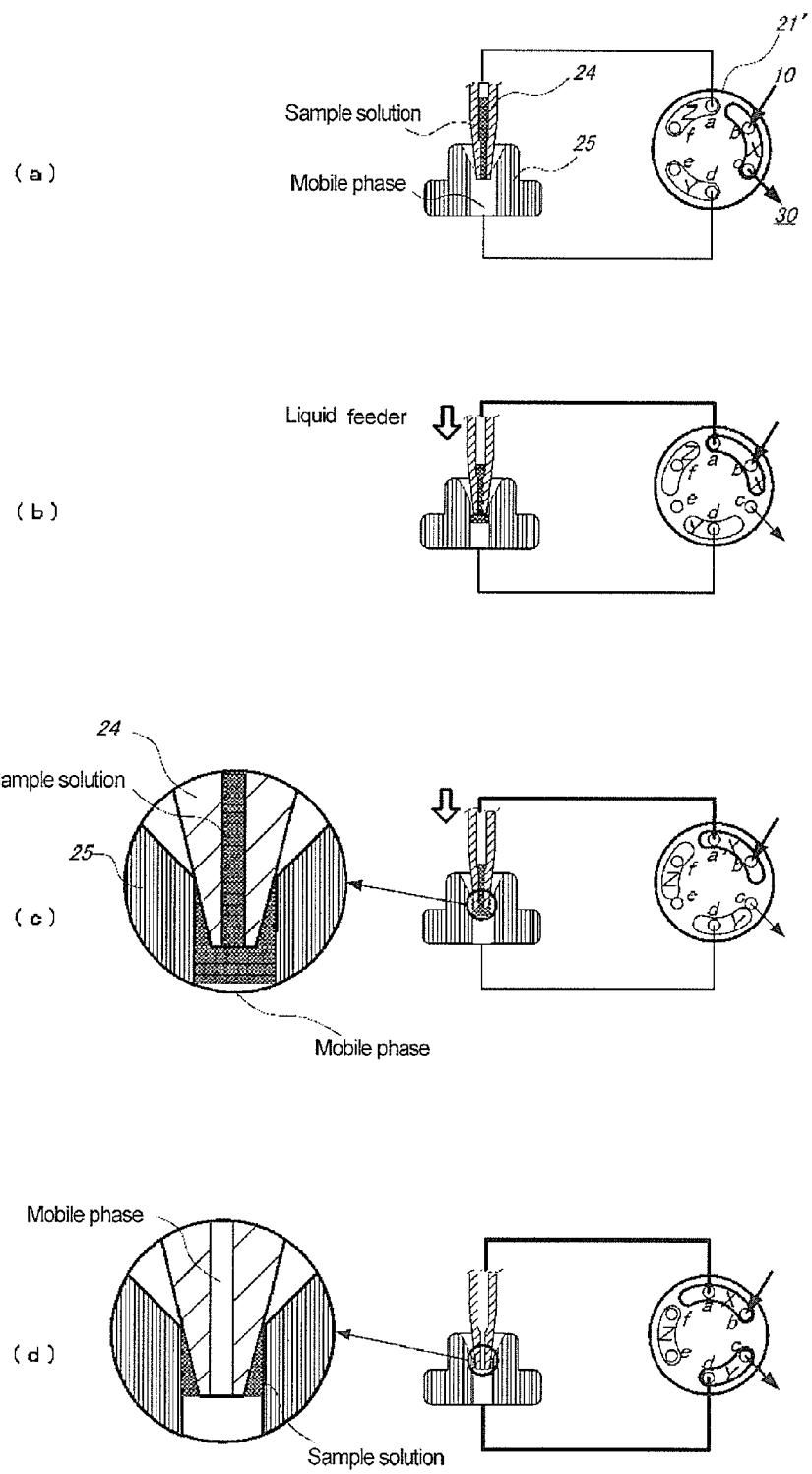
FIGS. 6(a) to 6(d) are diagrams illustrating a status of samples at an insertion section of a sampling and injection port in the sample introduction method in the prior art.

It can be seen from FIGS. 5(a) and 5(b) 5 that, for the sample introduction method in the prior art, an area α of a peak corresponding to the detected caffeine in the analysis of the caffeine aqueous solution is 3386603, an area β of a peak corresponding to the detected caffeine in the analysis of the blank sample is 229, and a carry-over volume β/α is 0.007%.

It can be seen from FIGS. 4(a) and 4(b) that, for the sample introduction method of the present invention, an area a of a peak corresponding to the detected caffeine in the analysis of the caffeine aqueous solution is 3237442, an area β of a peak corresponding to the detected caffeine in the analysis of the blank sample is 0 (undetectable), and a carry-over volume β/α is 0.000%. That is to say, the carry-over may not occur in the sample introduction method of the present invention.

In addition, the blank sample continues to be analyzed with respect to the sample introduction method in the prior art and the sample introduction method of the present invention. In the sample introduction method in the prior art, the area β is 118 for the second time, and the carry-over volume β/α is 0.002%. No peak corresponding to the caffeine is detected for the third time. Similarly, in the sample introduction method of the present invention, no peak is detected after the second time.

In view of the above, the carry-over is greatly reduced through the sample introduction method of the present invention. In addition, the sample introduction device used in the method of the present invention is the same as that disclosed in Registered Utility Model Patent No. 3129670 obtained by improving the device described in Japanese Patent Publication No. 2006-38809.

For the purpose of illustration, the flow path between the injection port 25 and the high pressure valve 21 is extended to avoid intersections of the flow paths in the figures. However, in order to shorten the analysis time or reduce the dead volumes, the flow path is preferably short. Alternatively, referring to the device disclosed in Japanese Patent Publication No. 2004-215118, the injection port 25 is directly disposed on the port of the high pressure valve 21. Moreover, it is clearly depicted in the figures that the sample loop 23 has a spiral section. Definitely, the sample loop 23 may also not have a spiral section, like the device disclosed in Japanese Patent Publication No. 2004-85499, as long as a required volume of the sample loop 23 is ensured. The method of the present invention is applicable to all the sample introduction devices disclosed in the aforementioned documents.

The above descriptions are merely an embodiment of the present invention, and modifications and variations can be made without departing from the scope of the invention. It should be understood that these modifications and variations also fall within the protection scope of the present invention.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sample introduction method, comprising:
   providing a sample introduction device comprising a flow path switching valve and a moving mechanism, wherein the flow path switching valve is connected to a flow path in communication with a liquid feeder for delivering a solution, a flow path in communication with a sample loop provided with the needle at a tip section of the sample loop, a flow path in communication with an analysis section for analyzing samples, and a flow path in communication with an injection port inserted with the needle, the flow path switching valve switches between the first status, in which the liquid feeder is in communication with the analysis section through the sample loop and the injection port, and the second status, in which, the liquid feeder is in communication with the analysis section not through the sample loop and the injection port, the moving mechanism enables the needle to move between the position for drawing samples and the injection port;
   switching the flow path switching valve from a first status to a second status;
   actuating the moving mechanism to move a needle to a position for drawing samples and draw a specified volume of samples with the needle;
   actuating the moving mechanism to move the needle to a position for drawing an intermediate liquid and draw a specified volume of intermediate liquid with the needle;
   actuating the moving mechanism to move the needle away from the position for drawing the intermediate liquid and insert the needle into an injection port; and
   performing an operation of drawing the samples inside the needle into the sample loop, before the moving mechanism is actuated to move the needle away from the position for drawing the intermediate liquid and insert the needle into the injection port.

2. The sample introduction method according to claim 1, wherein a drawn amount of the intermediate liquid is about 0.5% to 2% of an internal volume of the sample loop.

3. The sample introduction method according to claim 1, wherein the intermediate liquid different from the samples is drawn through the operation of drawing the samples in the needle into the sample loop.

4. A sample introduction method, the method comprising:
   providing a sample introduction device comprising a flow path switching valve, a cleaning port and a moving mechanism, wherein the flow path switching valve is connected to a flow path in communication with a liquid feeder for delivering a solution, a flow path in communication with a sample loop provided with the needle at a tip section, a flow path in communication with an analysis section for analyzing samples, and a flow path in communication with an injection port inserted with the needle, the flow path switching valve switches between the first status that the liquid feeder is in communication with the analysis section through the sample loop and the injection port, and the second status that the liquid feeder is in communication with the analysis section not through the sample loop and the injection port, a cleaning fluid is stored in the cleaning port for cleaning the needle, the moving mechanism enables the needle to move between the position for drawing samples, the injection port and the cleaning port;

switching the flow path switching valve from a first status to a second status;

actuating the moving mechanism to move a needle to a position for drawing samples and draw a specified volume of the samples with the needle;

actuating the moving mechanism to move the needle to a position for drawing an intermediate liquid and draw a specified volume of intermediate liquid with the needle;

actuating the moving mechanism to move the needle away from the position for drawing the intermediate liquid and insert the needle into an injection port; and performing an operation of drawing the samples inside the needle into the sample loop and moving the needle to the cleaning port to be cleaned, before the moving mechanism is actuated to move the needle away from the position for drawing the intermediate liquid and insert the needle into the injection port.

5. The sample introduction method according to claim 4, wherein the intermediate liquid different from the samples is drawn through the operation of drawing the samples in the needle into the sample loop.

6. The sample introduction method according to claim 4, wherein a drawn amount of the intermediate liquid is about 0.5% to 2% of an internal volume of the sample loop.

7. The sample introduction method according to claim 4, wherein the intermediate liquid is the same as a liquid in the cleaning port.

* * * * *